US009158132B1

(12) United States Patent
Cole et al.

(10) Patent No.: US 9,158,132 B1
(45) Date of Patent: Oct. 13, 2015

(54) DEFOGGING EYEWEAR ACCESSORY

(71) Applicants: Doug Cole, Maryville, TN (US); Marty Junior Caldwell, Corryton, TN (US)

(72) Inventors: Doug Cole, Maryville, TN (US); Marty Junior Caldwell, Corryton, TN (US)

( * ) Notice: Subject to any disclaimer, the term of this patent is extended or adjusted under 35 U.S.C. 154(b) by 0 days.

(21) Appl. No.: 14/253,174

(22) Filed: Apr. 15, 2014

(51) Int. Cl.
*G02C 11/08* (2006.01)
*A61F 9/02* (2006.01)

(52) U.S. Cl.
CPC .............. *G02C 11/08* (2013.01); *A61F 9/028* (2013.01)

(58) Field of Classification Search
CPC ................................ G02C 11/08; A61F 9/028
USPC .................. 351/62, 158; 2/435–437
See application file for complete search history.

(56) References Cited

U.S. PATENT DOCUMENTS

| 1,354,433 A | 9/1920 | De-Felice | |
| 2,099,464 A * | 11/1937 | Bruner et al. | 2/436 |
| 3,825,953 A * | 7/1974 | Hunter | 2/437 |
| 4,150,443 A | 4/1979 | McNeilly | |
| 5,452,480 A | 9/1995 | Ryden | |
| 2009/0276940 A1 | 11/2009 | Sallee | |
| 2012/0246808 A1 | 10/2012 | Spiro | |

FOREIGN PATENT DOCUMENTS

| GB | 2330916 | 5/1999 |
| WO | WO 94/07175 | 3/1994 |

* cited by examiner

*Primary Examiner* — Huy K Mai
(74) *Attorney, Agent, or Firm* — Kyle A. Fletcher, Esq.

(57) ABSTRACT

The defogging eyewear accessory includes a pneumatic pump, a tubing, and a distribution manifold that collectively form an accessory that is configured to dispel fog from eyewear. The distribution manifold is configured to attach onto eyewear via a clip member. The clip member clips onto the bridge of the eyewear in order to nozzles to dispense compressed air onto an interior surface of the lenses of said eyewear. The distribution manifold rests against the eyewear, and is adjacent to the bridge of an end user's nose. The tubing extends from the pneumatic pump to a connection port located on the distribution manifold. The device when in use shall dispel fog or other condensation from accumulating on the interior surface of the lenses of the eyewear in order to maintain a clear view through said eyewear.

17 Claims, 4 Drawing Sheets

DEFOGGING EYEWEAR ACCESSORY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of eyewear accessories, more specifically, an accessory configured for use with eyewear, and which defogs said eyewear.

SUMMARY OF THE INVENTION

An embodiment of the disclosure meets the needs presented above by generally comprising a pneumatic pump, a tubing, and a distribution manifold that collectively form an accessory that is configured to dispel fog from eyewear. The distribution manifold is configured to attach onto eyewear via a clip member. The clip member clips onto the bridge of the eyewear in order to nozzles to dispense compressed air onto an interior surface of the lenses of said eyewear. The distribution manifold rests against the eyewear, and is adjacent to the bridge of an end user's nose. The tubing extends from the pneumatic pump to a when in use shall dispel fog or other condensation from accumulating on the interior surface of the lenses of the eyewear in order to maintain a clear view through said eyewear.

These together with additional objects, features and advantages of the defogging eyewear accessory will be readily apparent to those of ordinary skill in the art upon reading the following detailed description of presently preferred, but nonetheless illustrative, embodiments of the defogging eyewear accessory when taken in conjunction with the accompanying drawings.

In this respect, before explaining the current embodiments of the defogging eyewear accessory in detail, it is to be understood that the defogging eyewear accessory is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the defogging eyewear accessory.

It is therefore important that the claims be regarded as including such equivalent construction insofar as they do not depart from the spirit and scope of the defogging eyewear accessory. It is also to be understood that the phraseology and terminology employed herein are for purposes of description and should not be regarded as limiting.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
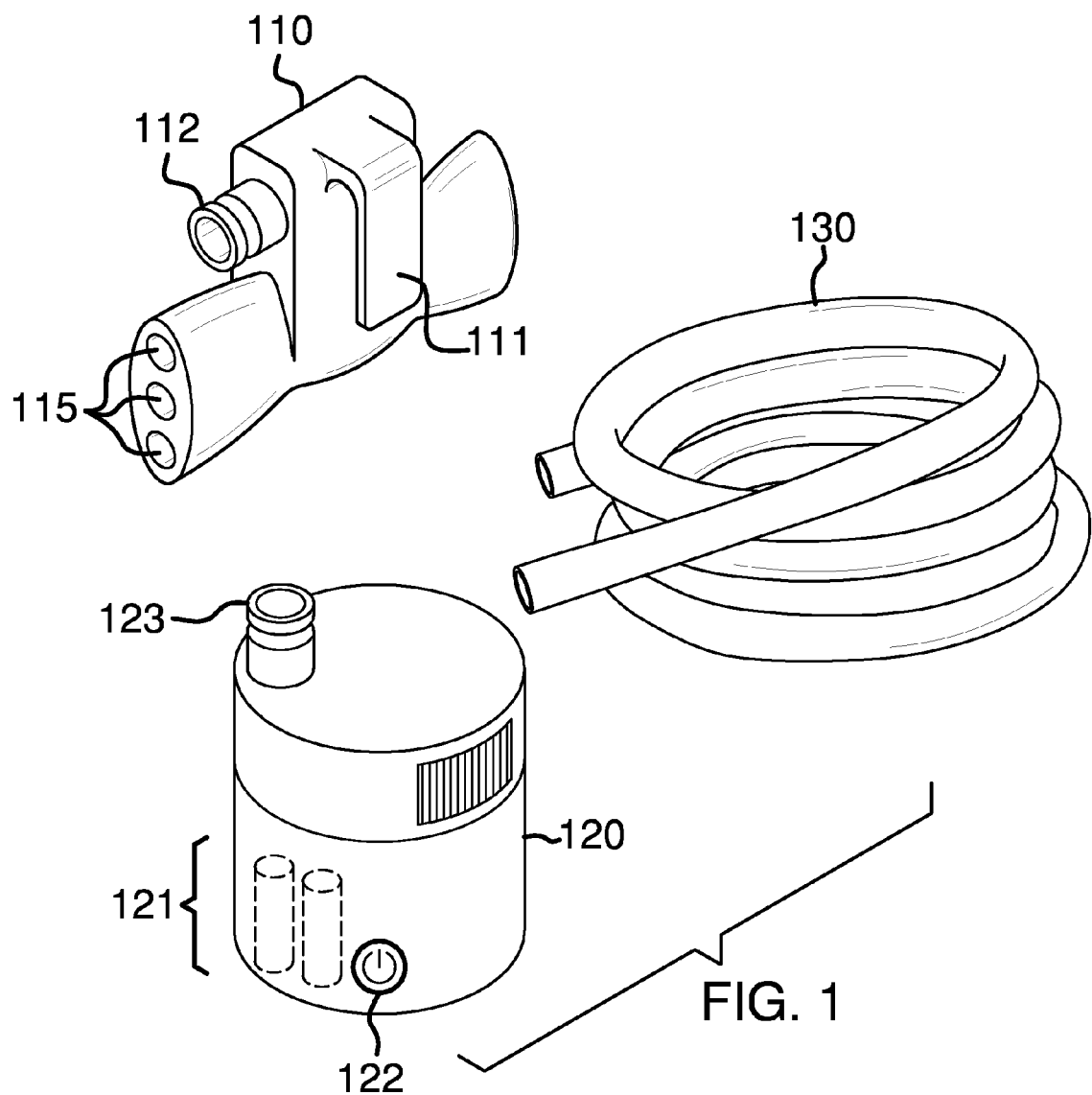
FIG. 1 is a view of the components comprising the defogging eyewear accessory.
Figure 2:
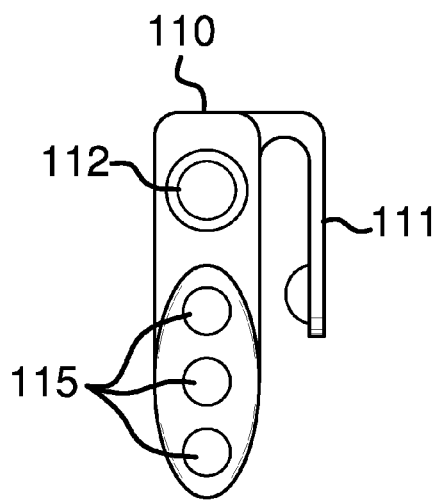
FIG. 2 is a side view of the distribution manifold.
Figure 3:
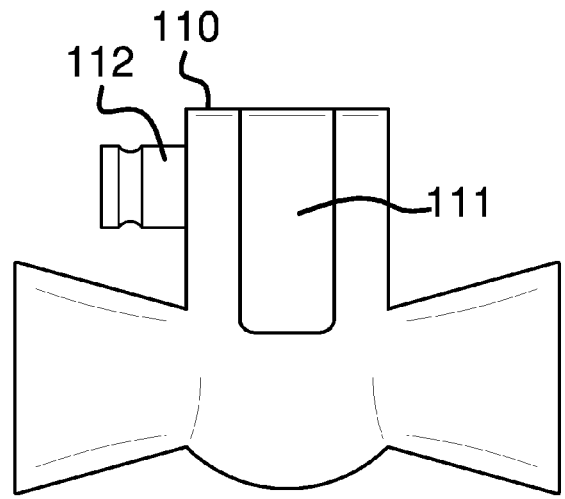
FIG. 3 is a front view of the distribution manifold.
Figure 4:
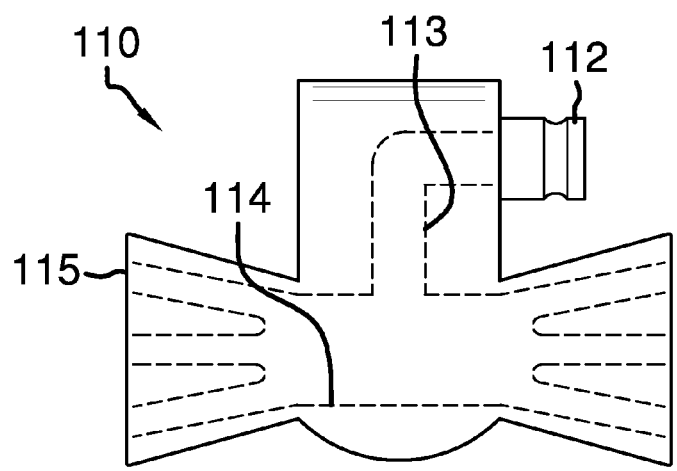
FIG. 4 is a view depicting the channels formed between the connection port and nozzles of the distribution manifold.
Figure 5:
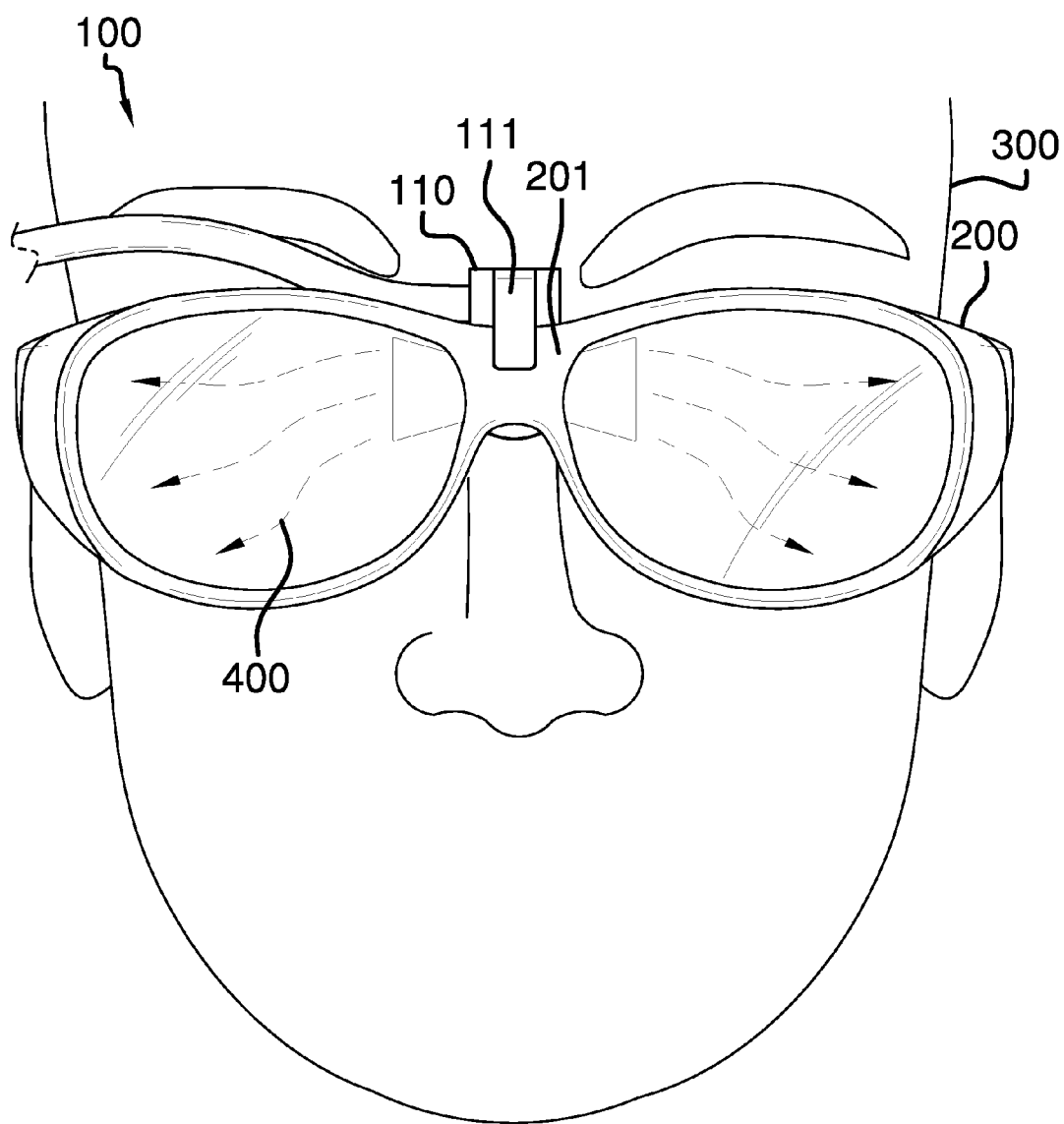
FIG. 5 is a front view of the defogging eyewear accessory in use.
Figure 6:
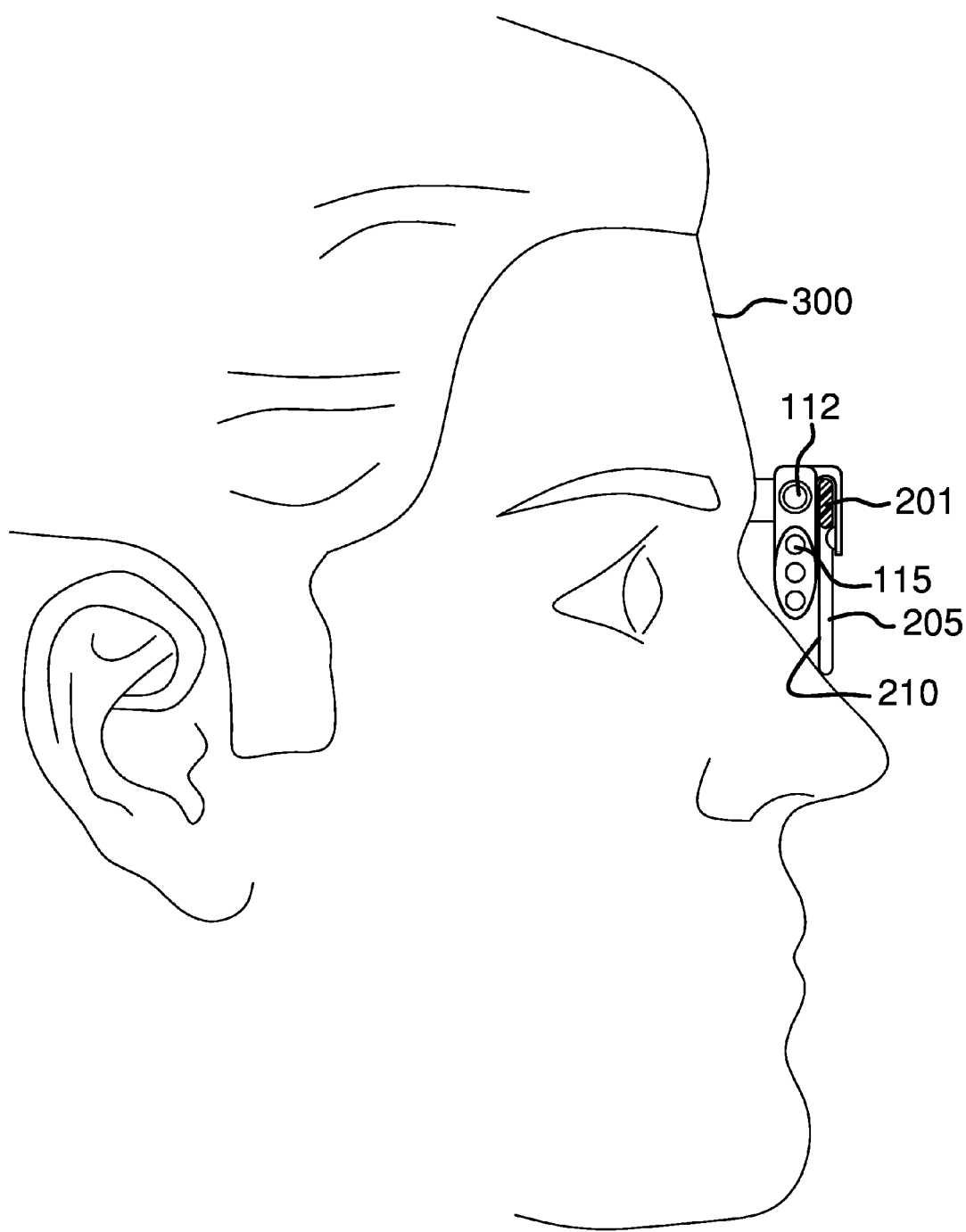
FIG. 6 is a side view of the defogging eyewear accessory in use.

As best illustrated in FIGS. 1 through 6, the defogging eyewear accessory 100 (hereinafter invention) generally comprises a distribution manifold 110, a pneumatic pump 120, and a tubing 130. The tubing 130 is responsible for transferring the output of the pneumatic pump 120 to the distribution manifold 110. Moreover, the tubing 130 is of an undefined diameter and an undefined length, and is made of a flexible material suitable for transferring compressed air.

The pneumatic pump 120 is portably powered, which means that a powering member 121 is located inside of the pneumatic pump 120. The powering member 121 is ideally composed of at least one battery that is rechargeable. The pneumatic pump 120 includes an on/off button 122 that turns the pneumatic pump 120 on or off. The pneumatic pump 120 includes a pump outlet 123 that is able to connect with the tubing 130.

The invention 100 is designed to enable compressed air to extend from the pneumatic pump 120 to the distribution manifold 110. The distribution manifold 110 is configured to attach onto eyewear 200. Moreover, the distribution manifold 110 includes a clip member 111 that is able to clip onto a bridge portion 201 of the eyewear 200. Moreover, the distribution manifold 110 is located in between the eyewear 200 and an end user 300.

The distribution manifold 110 is further defined with a connection port 112 that is able to connect with the tubing 130. The distribution manifold 110 includes a first channel 113 that extends from the connection port 112 to a manifold chamber 114. The manifold chamber 114 is centrally located with respect to the distribution manifold 110. The manifold chamber 114 connects the first channel 113 as well as the connection port 112 to a plurality of air nozzles 115. The air nozzles 115 direct compressed air 400 to the left and to the right of the distribution manifold 110. Moreover, the air nozzles 115 direct the compressed air 400 to an interior surface 210 of lenses 205 of the eyewear 200 in order to expel or prevent condensation from occurring on the eyewear 200.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A defogging eyewear accessory comprising:
   a distribution manifold configured to attach onto a bridge of eyewear in order to direct compressed air onto an interior surface of lenses of said eyewear thereby preventing and expelling condensation thereon;
   a tubing connects to the distribution manifold and a pneumatic pump in order to transport said compressed air from said pneumatic pump to said distribution manifold.

2. The defogging eyewear accessory according to claim 1 wherein the pneumatic pump is portably powered via a powering member located inside of the pneumatic pump.

3. The defogging eyewear accessory according to claim 2 wherein the pneumatic pump includes an on/off button that turns the pneumatic pump on or off; wherein the pneumatic pump includes a pump outlet that is able to connect with the tubing.

4. The defogging eyewear accessory according to claim 3 wherein the distribution manifold includes a clip member that is able to clip onto a bridge portion of the eyewear.

5. The defogging eyewear accessory according to claim 4 wherein the distribution manifold is located in between the eyewear and an end user.

6. The defogging eyewear accessory according to claim 5 wherein the distribution manifold is further defined with a connection port that is able to connect with the tubing.

7. The defogging eyewear accessory according to claim 6 wherein the distribution manifold includes a first channel that extends from the connection port to a manifold chamber.

8. The defogging eyewear accessory according to claim 7 wherein the manifold chamber is centrally located with respect to the distribution manifold.

9. The defogging eyewear accessory according to claim 8 wherein the manifold chamber connects the first channel as well as the connection port to a plurality of air nozzles.

10. The defogging eyewear accessory according to claim 9 wherein the air nozzles direct compressed air to the left and to the right of the distribution manifold.

11. A defogging eyewear accessory comprising:
    a distribution manifold configured to attach onto a bridge of eyewear in order to direct compressed air onto an interior surface of lenses of said eyewear thereby preventing and expelling condensation thereon;
    a tubing connects to the distribution manifold and a pneumatic pump in order to transport said compressed air from said pneumatic pump to said distribution manifold;
    wherein the pneumatic pump is portably powered via a powering member located inside of the pneumatic pump;
    wherein the pneumatic pump includes an on/off button that turns the pneumatic pump on or off; wherein the pneumatic pump includes a pump outlet that is able to connect with the tubing;
    wherein the distribution manifold includes a clip member that is able to clip onto a bridge portion of the eyewear.

12. The defogging eyewear accessory according to claim 11 wherein the distribution manifold is located in between the eyewear and an end user.

13. The defogging eyewear accessory according to claim 12 wherein the distribution manifold is further defined with a connection port that is able to connect with the tubing.

14. The defogging eyewear accessory according to claim 13 wherein the distribution manifold includes a first channel that extends from the connection port to a manifold chamber.

15. The defogging eyewear accessory according to claim 14 wherein the manifold chamber is centrally located with respect to the distribution manifold.

16. The defogging eyewear accessory according to claim 15 wherein the manifold chamber connects the first channel as well as the connection port to a plurality of air nozzles.

17. The defogging eyewear accessory according to claim 16 wherein the air nozzles direct compressed air to the left and to the right of the distribution manifold.

\* \* \* \* \*